(12) United States Patent
Denney et al.

(10) Patent No.: US 6,274,578 B1
(45) Date of Patent: Aug. 14, 2001

(54) SPLA$_2$ INHIBITOR ESTER

(75) Inventors: Michael Lyle Denney, Franklin; John Michael Morin, Brownsburg; Daniel Jon Sall; Jason Scott Sawyer, both of Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/673,677
(22) PCT Filed: Apr. 20, 1999
(86) PCT No.: PCT/US99/08538
   § 371 Date: Oct. 17, 2000
   § 102(e) Date: Oct. 17, 2000
(87) PCT Pub. No.: WO99/56752
   PCT Pub. Date: Nov. 11, 1999
(51) Int. Cl.$^7$ ............ A61K 31/5377; A61P 11/06; C07D 413/12
(52) U.S. Cl. ......................... 514/235.2; 544/144
(58) Field of Search .................. 544/144; 514/235.2

(56) References Cited

U.S. PATENT DOCUMENTS

| 5,654,326 | 8/1997 | Bach . |
| 6,140,327 | 10/2000 | Sawyer . |
| 6,177,426 | 1/2001 | Denney . |

FOREIGN PATENT DOCUMENTS

| WO 98/42343 | 10/1998 | (WO) . |
| WO 99/21559 | 5/1999 | (WO) . |
| WO 99/25339 | 5/1999 | (WO) . |

OTHER PUBLICATIONS

Denny et al, *Chemical Abstracts*, vol. 130, No. 311, 696 (1999).*

Lipsky, James J., The Lancet, vol. 348, pp. 1357–1359, Nov. 16, 1996.

* cited by examiner

*Primary Examiner*—Robert W. Ramsuer
(74) *Attorney, Agent, or Firm*—Roger S. Benjamin

(57) ABSTRACT

The compound, ((3(2-amino-1,2-dioxoethyl)-2-methyl-1-(phenylmethyl)-1H-indol-4-yl)oxy)acetic acid N-morpholino ester, is disclosed together with its use as a highly bioavailable indole sPLA$_2$ inhibitor compound.

2 Claims, No Drawings

SPLA₂ INHIBITOR ESTER

FIELD OF THE INVENTION

This application is a 371 of PCT/US 99/08538 filed Apr. 20, 1999.

This invention relates to an sPLA₂ inhibitor compound having high bioavailability.

BACKGROUND OF THE INVENTION

The structure and physical properties of human non-pancreatic secretory phospholipase A₂ (hereinafter called, "sPLA₂") has been thoroughly described in two articles, namely, "Cloning and Recombinant Expression of Phospholipase A₂ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol . 264, No. 10, Issue of Apr. 5, 1989; pp. 5335–5338, and "Structure and Properties of a Human Non-pancreatic Phospholipase A₂" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, 1989; pp. 5768–5775, the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid) and are highly bioavailable in mammals, especially humans. Such compounds are of value in general treatment of conditions induced and/or maintained by overproduction of sPLA₂; such as septic shock, adult respiratory distress syndrome, pancreatitis, trauma, bronchial asthma, allergic rhinitis, rheumatoid arthritis, etc.

Therapeutic agents that may be given orally are, in general, greatly preferred and have enhanced commercial potential because of their inherent ease of use.

U.S. Pat. No. 5,654,326 describes certain indole type sPLA₂ inhibitors and related ester prodrugs. In particular, this patent exemplifies the methyl ester of ((3-(2-amino-1,2-dioxoethyl)-2-methyl-1-(phenylmethyl)-1H-indol-4-yl)oxy)acetic acid.

It is desirable to develop more highly available sPLA₂ inhibitors, particularly those suitable for oral administration.

SUMMARY OF THE INVENTION

This invention is the novel compound, ((3-(2-amino-1,2-dioxoethyl)-2-methyl-1-(phenylmethyl)-1H-indol-4-yl)oxy)acetic acid N-morpholino ethyl ester; which is highly bioavailable by oral administration.

This invention is a pharmaceutical formulation comprising ((3-(2-amino-1,2-dioxoethyl)-2-methyl-1-(phenylmethyl)-1H-indol-4-yl)oxy)acetic acid, N-morpholino ethyl ester in combination with a carrier or diluent.

DETAILED DESCRIPTION OF THE INVENTION

The 1H-Indole-3-Glyoxylamide Compound of the Invention

The compound of the invention((3-(2-amino-1,2-dioxoethyl)-2-methyl-1-(phenylmethyl)-1H-indol-4-yl)oxy) acetic acid, N-morpholino ethyl ester; is represented by the structural formula (I);

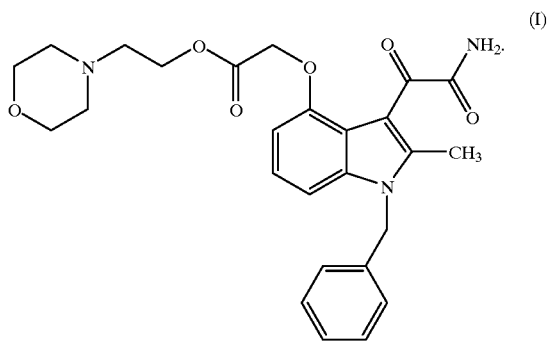

The N-morpholino ethyl ester (I) is an ester form of known sPLA₂ inhibitor ((3-(2-amino-1,2-dioxoethyl)-2-methyl-1-(phenylmethyl)-1H-indol-4-yl)oxy)acetic acid, represented by the structural formula (II), below;

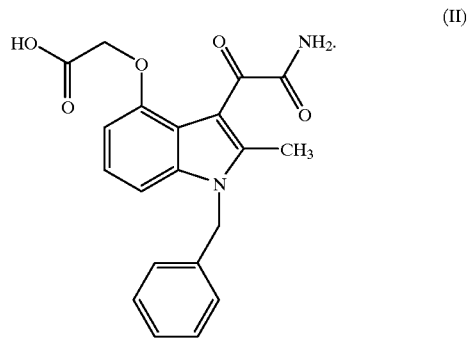

The compound of formula (II) is described in Example 1 of U.S. Pat. No. 5,654,326 (the disclosure of which is incorporated herein by reference) and European Patent Application No. 95302166.4, Publication No. 0 675 110 (publ., Oct. 4, 1995).

It is a discovery of this invention that the compound of formula (I) is highly bioavailable upon oral administration compared to other sPLA₂ inhibitors.

Synthesis of the Compound of the Invention

The synthesis of ((3-(2-amino-1,2-dioxoethyl)-2-methyl-1-(phenylmethyl)-1H-indol-4-yl)oxy)acetic acid, N-morpholino ethyl ester (compound of formula I, supra.) uses as starting material ((3-(2-amino-1,2-dioxoethyl)-2-methyl-1-(phenylmethyl)-1H-indol-4-yl)oxy)acetic acid, or a salt thereof (compound of formula II, supra.). This starting material may be prepared by the reaction schemes or method of Example 1 of U.S. Pat. No. 5,654,326 (the disclosure of which is incorporated herein by reference). Similar methods are shown in European Patent Application No. 95302166.4, Publication No. 0 675 110 (publ., Oct. 4, 1995). Other conventional methods may also be used for preparing the starting material. Procedures useful for the synthesis of the compound of this invention are specified in Example 1 set out below:

EXAMPLE 1

Preparation of ((3-(2-Amino-1,2-dioxoethyl)-2-methyl-1-(phenylmethyl)-1H-indol-4-yl)oxy)acetic acid, N-morpholino ethyl ester, a compound represented by the formula:

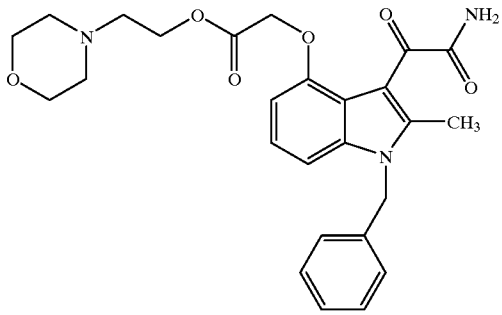

Part A
Preparation of N-tert-butoxycarbonyl-3-methoxy-2-methylaniline.

A solution of 44.4 g (344 mmol) of 3-methoxy-2-methylaniline and 75 g (344 mmol) of di-tert-butyl dicarbonate in 400 mL of THF was heated to maintain reflux for 4 hours. After concentrating at reduced pressure, the residue was taken up in ethyl acetate, washed with iN citric acid, water and dried (MgSO$_4$). After removing the solvent at reduced pressure, the residue was crystallized from hexane to give 64.5 g (84% yield) of N-tert-butoxycarbonyl-3-methoxy-2-methylaniline, mp, 56–57° C.

Analysis for $C_{13}H_{19}NO_3$:
Calculated: C, 65.80; H, 8.07; N, 5.90
Found: C, 63.32; H, 7.83; N, 5.56.

Part B
Preparation of 4-Methoxy-2-methyl-1H-indole.

A solution of 280 mL (0.36 mol) of 1.3M sec-butyl lithium in cyclohexane was added slowly to N-tert-butoxycarbonyl-3-methoxy-2-methylaniline (43 g, 0.18 mol) in 300 mL of THF keeping the temperature below −40° C. with a dry ice-ethanol bath. The bath was removed and the temperature allowed to rise to −20° C. and then the bath replaced. After the temperature had cooled to −60° C., 18.5 g (0.18 mol) of N-methoxy-N-methylglyoxylamide in an equal volume of THF was added dropwise. The reaction mixture was stirred 1 hour, the cooling bath removed and stirred an additional 1 hour. It was then poured into a mixture of 600 mL of ether and 600 mL of 1N HCl. The organic layer was separated, washed with water, dried over MgSO$_4$, and concentrated at reduced pressure to give 39.5 g of a mixture of 1-(2-(tert-butoxycarbonylamino)-6-methoxyphenyl)-2-propanone and starting anilide. This mixture was dissolved in 100 mL of methylene chloride and 40 mL of trifluoroacetic acid and stirred for a total of 26 hours. The mixture was washed with water, dried(MgSO$_4$) and concentrated at reduced pressure. The residue was chromatographed on silica gel eluting with 20% EtOAc/hexane to give on crystallization from CH$_2$Cl$_2$/hexane 13.9 g of 4-methoxy-2-methyl-1H-indole, mp, 80–86° C.

Analysis for $C_{10}H_{11}NO$:
Calculated: C, 74.51; H, 6.88; N, 8.69
Found: C, 74.41; H, 7.08; N, 8.47.

Part C
Preparation of 4-Methoxy-2-methyl-1-(phenylmethyl)-1H-indole.

4-Methoxy-2-methyl-1H-indole (1 g, 6.2 mmol) was added to 248 mg (6.2 mmol) of 60% sodium hydride/mineral oil (washed with hexane before adding DMF) in 15 mL of DMF and after stirring for 0.5 hour, 0.74 mL (6.2 mmol) of benzyl bromide was added. The mixture was stirred at room temperature for 18 hours, diluted with water and extracted with ethyl acetate. The ethyl acetate solution was washed with brine, dried (MgSO$_4$) and after concentrating at reduced pressure, the residue was chromatographed on silica gel eluting with 20% EtOAc/hexane to give 1.3 g(84% yield) of 4-methoxy-2-methyl-1-(phenylmethyl)-1H-indole, melting at 96–116° C.

Analyses for $C_{17}H_{17}NO$: Calculated: C, 81.24; H, 6.82; N, 5.57 Found: C, 81.33; H, 6.74; N, 5.29.

Part D
Preparation of 4-Hydroxy-2-methyl-1-(phenylmethyl)-1H-indole.

A solution of 1.25 g (5 mmol) of 4-methoxy-2-methyl-1-(phenylmethyl)-1H-indole and 20 mL of 1M BBr$_3$/CH$_2$Cl$_2$ in 50 mL of methylene chloride was stirred at room temperature for 5 hours and concentrated at reduced pressure. The residue was dissolved in ethyl acetate, washed with brine and dried (MgSO$_4$). After concentrating at reduced pressure, the residue was chromatographed on silica gel eluting with 20% EtOAc/hexane to give 577 mg (49% yield) of 4-hydroxy-2-methyl-1- (phenylmethyl)-1H-indole, 125–127° C.

Analyses for $C_{16}H_{15}NO$: Calculated: C, 80.98; H, 6.37; N, 5.90 Found: C, 80.76; H, 6.26; N, 5.80.

Part E
Preparation of ((2-Methyl-1-(phenylmethyl)-1H-indol-4-yl)oxy)acetic acid methyl ester.

4-Hydroxy-2-methyl-1-(phenylmethyl)-1H-indole (530 mg, 2.2 mmol) was added to 88 mg (2.2 mmol) of 60% NaH/mineral oil in 20 mL of DMF and the mixture stirred for 0.67 hours. Then, 0.21 mL (2.2 mmol) of methyl bromoacetate was added and stirring maintained for 17 hours. The mixture was diluted with water and extracted with ethyl acetate. The ethyl acetate solution was washed with brine, dried (MgSO$_4$), and concentrated at reduced pressure. The residue was chromatographed on silica gel eluting with 20% EtOAc/hexane to give 597 mg (88% yield) of ((2-methyl-1-(phenylmethyl)-1H-indol-4-yl)oxy)acetic acid methyl ester, 140–143° C.

Analyses for $C_{19}H_{19}NO_3$: Calculated: C, 73.77; H, 6.19; N, 4.53 Found: C, 74.01; H, 6.23; N, 4.32.

Part F
Preparation of ((3-(2-Amino-1,2-dioxoethyl)-2-methyl-1-(phenylmethyl)-1H-indol-4-yl)oxy) acetic acid methyl ester.

Oxalyl chloride (0.16 mL, 1.9 mmol) was added to 582 mg (1.9 mmol) of ((2-methyl-1-(phenylmethyl)-1H-indol-4-yl)oxy)acetic acid methyl ester in 10 mL of methylene chloride and the mixture stirred for 1.5 hours. The mixture was concentrated at reduced pressure and residue taken up in 10 mL of methylene chloride. Anhydrous ammonia was bubbled in for 0.25 hours, the mixture stirred for 1.5 hours and evaporated at reduced pressure. The residue was stirred with 20 mL of ethyl acetate and the mixture filtered. The filtrate was concentrated to give 672 mg of a mixture of ((3-(2-amino-1,2-dioxoethyl)-2-methyl-1-(phenylmethyl)-1H-indol-4-yl)oxy)acetic acid, methyl ester and ammonium chloride, mp 202–215° C.

Part G
Preparation of ((3-(2-Amino-1,2-dioxoethyl)-2-methyl-1-(phenylmethyl)-1H-indol-4-yl)oxy)acetic acid.

A mixture of 660 mg (1.7 mmol) of ((3-(2-amino-1,2-dioxoethyl)-2-methyl-1-(phenylmethyl)-1H-indol-4-yl)oxy) acetic acid methyl ester and 10 mL of 1N NaOH in 30 mL of methanol was heated to maintain reflux for 1 hour, cooled to room temperature and stirred for 0.5 hour. The mixture was concentrated at reduced pressure and the residue taken up in EtOAc/water. The aqueous layer was separated, made acidic to pH 2–3 with 1N HCl and extracted with EtOAc. On concentrating the EtOAc solution, 431 mg (69% yield) of ((3-(2-amino-1,2-dioxoethyl)-2-methyl-1-(phenylmethyl)-1H-indol-4-yl)oxy)acetic acid crystallized, melting at 218–220° C.

Analyses for $C_{20}H_{18}N_2O_5$: Calculated: C, 65.57; H, 4.95; N, 7.65 Found: C, 63.31; H, 4.79; N, 6.91.

Part H

Preparation of ((3-(2-amino-1,2-dioxoethyl)-2-methyl-1-(phenylmethyl)-1H-indol-4-yl)oxy) acetic acid N-morpholino ethyl ester.

The compound of the present invention may be formed by the reaction of 4-(2-chloroethyl)morpholine hydrochloride (available from Aldrich Chemical Co., Milwaukee, Wis. USA, Item No. C4,220–3) and suitable base preferably $Cs_2CO_3$; and ((3-(2-amino-1,2-dioxoethyl)-2-methyl-1-(phenylmethyl)-1H-indol-4-yl)oxy)acetic acid, sodium salt in a suitable solvent, preferably dimethylformamide. The slurry should be heated to 60° C. or other appropriate temperature until a solution is formed. Heating should continued until the reaction is complete. The reaction mixture should be worked up to isolate the product using conventional organic laboratory techniques.

Assay 1

Cynomolgus monkeys were used in a single dose pharmacokinetic study. The monkeys (3 per treatment) were administered a single oral 10 mg/kg dose of one of six indole prodrug compounds including the compound of this invention.

Serial blood samples were obtained up to 24 hours after dose administration. Plasma was analyzed for the corresponding free acid using an LC/MS method. Also area under the curve (auc) values were computed at 8 and 24 hours.

The purpose of this assay was to evaluate and compare the oral delivery for selected $sPLA_2$ inhibitors.
Test Subject:
  Species: Monkeys
  Strain: Cynomolgus
Dose Preparation:
  The amount of $sPLA_2$ inhibitor was corrected for free acid equivalents.
Vehicle:
  Suspension of $sPLA_2$ inhibitor in 10% Acacia, prepared just prior to dose administration
Dose Administration:
  Route: Oral
  Frequency: Single dose
  Dose: 10 mg/kg (of the parent acid)
  Dosage Volume: 5 mL/kg

TABLE 1

Results
Monkey Pharmacokinetics Study

| Compound ester type | Cmax (ng/ml) | Tmax hours | AUC (0–8 hr) ng*h/ml | AUC (0–24 hr) ng*h/ml |
|---|---|---|---|---|
| 1 | 1604 | 2.0 | 5131 | 5425 |
| 2 | 200 | 2.0 | 1356 | 2038 |
| 3 | 213 | 2.0 | 1277 | 1761 |
| 4 | 245 | 2.0 | 1675 | 3404 |
| 5 | 3296 | 2.0 | 11919 | 13161 |
| 6 | 615 | 3.3 | — | 8730 |

TABLE 1-continued

Results
Monkey Pharmacokinetics Study

| Compound ester type | Cmax (ng/ml) | Tmax hours | AUC (0–8 hr) ng*h/ml | AUC (0–24 hr) ng*h/ml |
|---|---|---|---|---|

1 = ((3-(2-amino-1,2-dioxoethyl)-2-methyl-1-(phenylmethyl)-1H-indol-4-yl)oxy)acetic acid N-morpholino ethyl ester
2 = ((3-(2-amino-1,2-dioxoethyl)-2-methyl-1-(phenylmethyl)-1H-indol-4-yl)oxy)acetic acid methyl ester
3 = ((3-(2-Amino-1,2-dioxoethyl)-1-((1,1'-biphenyl)-2-ylmethyl)-2-methyl-1H-indol-4-yl)oxy)acetic acid N,N-diethylglycolamido ester
4 = ((3-(2-Amino-1,2-dioxoethyl)-2-ethyl-1-(phenylmethyl)-1H-indol-4-yl)oxy)acetic acid ethyl ester
5 = ((3-(2-Amino-1,2-dioxoethyl)-2-ethyl-1-(phenylmethyl)-1H-indol-4-yl)oxy)acetic acid N-morpholino ethyl ester
6 = ((3-(2-Amino-1,2-dioxoethyl)-2-ethyl-1-(phenylmethyl)-1H-indol-4-yl)oxy)acetic acid methyl ester Assay II The bioavailability of the compound of the invention, ((3-(2-amino-1,2-dioxoethyl)-2-methyl-1-(phenylmethyl)-1H-indol-4-yl)oxy)acetic acid-N-morpholino ethyl ester, was also determined using a Rat Plasma single dose oral Pharmacokinetics Study:

The purpose of this assay was to evaluate and compare the oral delivery for selected $sPLA_2$ inhibitors.
Test Subject:
  Species: Rat
  Strain: Fischer 344
Dose Preparation:
  The amount of $sPLA_2$ inhibitor was corrected for free acid equivalents.
Vehicle:
  Suspension of $sPLA_2$ inhibitor in 10% Acacia, prepared just prior to dose administration
Dose Administration:
  Route: Oral
  Frequency: Single dose
  Dose: 10 mg/kg (of the parent acid)
  Dosage Volume: 5 mL/kg
  Rats fasted overnight.
Specimen Collection:
  Blood samples (0.8 ml) were obtained at the following times: 0.5, 1, 2, 4, 6 and 8 hours (2 rats/timepoint)
Data Analysis:
  Plasma was assayed by HPLC to measure concentrations of the different $sPLA_2$ inhibitors (as free acids).
  Cmax (maximal plasma concentrations), and AUC values were determined from the mean plasma concentration-time profiles.

TABLE 2

| Compound ester type | Cmax (ng/ml) | AUC (0–8 hr) |
|---|---|---|
| 11 | 1094 | 2400 |
| 12 | 79 | 385 |
| 13 | 258 | 1229 |
| 14 | 1199 | 2604 |
| 15 | 612 | 1504 |
| 16 | 259 | 1031 |

11 = ((3-(2-amino-1,2-dioxoethyl)-2-methyl-1-(phenylmethyl)-1H-indol-4-yl)oxy)acetic acid N-morpholino ethyl ester (compound of the invention)
12 = ((3-(2-Amino-1,2-dioxoethyl)-2-methyl-1-(phenylmethyl)-1H-indol-4-yl)oxy)acetic acid N,N-diethylacetamido ester TABLE 2-continued

| Compound ester type | Cmax (ng/ml) | AUC (0–8 hr) |
|---|---|---|

13 = ((3-(2-Amino-1,2-dioxoethyl)-2-methyl-1-((1-naphthalenyl)methyl)-1H-indol-4-yl)oxy)acetic acid N,N-diethylacetamido ester
14 = ((3-(2-Amino-1,2-dioxoethyl)-2-methyl-1-((1-naphthalenyl)methyl)-1H-indol-4-yl)oxy)acetic acid morpholino N-ethyl ester
15 = ((3-(2-Amino-1,2-dioxoethyl)-2-ethyl-1-((3-chlorophenyl)methyl)-1H-indol-4-yl)oxy)acetic acid N-morpholino ethyl ester
16 = ((3-(2-Amino-1,2-dioxoethyl)-2-ethyl-1-((3-chlorophenyl)methyl)-1H-indol-4-yl)oxy)acetic acid N,N-diethylacetamido ester While the present invention has been illustrated above by certain specific embodiments, it is not intended that these specific examples should limit the scope of the invention as described in the appended claims.

We claim:

1. The compound, ((3-(2-amino-1,2-dioxoethyl)-2-methyl-1-(phenylmethyl)-1H-indol-4-yl)oxy)acetic acid N-morpholino ethyl ester.

2. A pharmaceutical formulation comprising the compound of claim 1 in combination with a carrier or diluent.

* * * * *